（12）United States Patent
Liu et al.

(10) Patent No.: US 11,786,303 B2
(45) Date of Patent: Oct. 17, 2023

(54) MICROWAVE ABLATION PROBE

(71) Applicant: Quicker-Instrument Inc., Richmond (CA)

(72) Inventors: Binghui Liu, Richmond (CA); Ting Yang, Richmond (CA); Ye Liang, Richmond (CA); Yixin Yang, Richmond (CA); Yongfan Ke, Richmond (CA); Zhao Chun Chen, Richmond (CA)

(73) Assignee: QUICKER-INSTRUMENT INC., Richmond (CA)

( * ) Notice: Subject to any disclaimer, the term of this patent is extended or adjusted under 35 U.S.C. 154(b) by 290 days.

(21) Appl. No.: 17/206,610

(22) Filed: Mar. 19, 2021

(65) Prior Publication Data

US 2022/0296298 A1 Sep. 22, 2022

(51) Int. Cl.
*A61B 18/18* (2006.01)
*A61B 18/00* (2006.01)

(52) U.S. Cl.
CPC ............ *A61B 18/1815* (2013.01); *A61B 2018/00077* (2013.01); *A61B 2018/00083* (2013.01); *A61B 2018/00315* (2013.01); *A61B 2018/00577* (2013.01); *A61B 2018/183* (2013.01); *A61B 2018/1823* (2013.01)

(58) Field of Classification Search
CPC . A61B 18/1815; A61B 18/18; A61B 18/1492; A61B 2018/183; A61B 2018/1838; A61B 2018/1853; A61B 2018/00875; A61B 2018/1846; A61B 2018/00577; A61B 2018/00077; A61B 2018/00083; A61B 2018/1823;
(Continued)

(56) References Cited

U.S. PATENT DOCUMENTS 4,700,716 A * 10/1987 Kasevich ............... A61B 18/18
607/156
5,904,709 A * 5/1999 Arndt ................. A61B 18/1815
607/101
(Continued)

OTHER PUBLICATIONS

Examination report from Canadian Patent Office dated Jan. 18, 2023.

*Primary Examiner* — Khadijeh A Vahdat
*Assistant Examiner* — Marina Delaney Templeton

(57) ABSTRACT

Examples of a probe for microwave ablation are disclosed. The probe comprises a feed coaxial cable and an antenna that has a cylindrical outer housing with a predetermined diameter and a predetermined length defining a cavity therein and a radiating conductor positioned within the cavity with a matching stepped portion. The antenna further comprises a dielectric material placed in the cavity between the radiating conductor and the outer housing of the antenna to increase the mechanical strength of the probe as well as to improve the power coupling to the tissue to be ablated. The design of the coaxial cavity of the antenna with radiating conductor with a stepped portion fitted into dielectric materials increases antenna's mechanical strength to withstand higher temperatures and reduces an energy reflected back to the feed coaxial cable due to a good impedance match between the antenna and the feed cable such that antennas with smaller length can be used to fit curved paths.

14 Claims, 3 Drawing Sheets

(58) Field of Classification Search
CPC .... A61B 2018/1861; A61B 2018/1869; A61B 2018/1876; A61B 2018/1892
See application file for complete search history.

(56) References Cited

U.S. PATENT DOCUMENTS

| | | | | |
|---|---|---|---|---|
| 6,277,113 | B1 * | 8/2001 | Berube | A61B 18/1492 607/101 |
| 7,128,739 | B2 * | 10/2006 | Prakash | A61B 18/18 606/41 |
| 2006/0293651 | A1 * | 12/2006 | Cronin | A61B 18/18 607/101 |
| 2009/0005766 | A1 * | 1/2009 | Brannan | A61B 18/1815 606/10 |
| 2010/0228244 | A1 * | 9/2010 | Hancock | A61B 18/1815 606/33 |
| 2011/0118720 | A1 * | 5/2011 | Turner | A61B 18/1815 606/33 |
| 2014/0290830 | A1 | 10/2014 | Brannan | |
| 2014/0296839 | A1 * | 10/2014 | Brannan | A61B 18/1815 606/33 |
| 2016/0000505 | A1 * | 1/2016 | Cronin | A61B 18/1815 606/33 |
| 2021/0052317 | A1 * | 2/2021 | Hancock | A61B 18/1206 |

* cited by examiner

MICROWAVE ABLATION PROBE

TECHNICAL FIELD

The present disclosure generally relates to a microwave ablation probe and more particular to a short and high efficiency ablation probe.

BACKGROUND

Unless otherwise indicated herein, the materials described in this section are not prior art to the claims in this application and are not admitted to be prior art by inclusion in this section.

Microwave ablation is a form of thermal ablation that uses electromagnetic waves in the microwave energy spectrum to locally heat the tissue and cause tissue necrosis. Microwave ablation probes are usually used in the treatment of solid tumors as well as the treatment of varicose veins, reticular or spider veins.

Spider veins, reticular veins and varicose veins are common conditions that occur in many humans and are typically found in the limbs of the human body, in particular in the legs. Spider veins (i.e., telangiectasia) are small, dilated blood vessels near the surface of the skin. They can develop anywhere on the body but commonly are found on the face, around the nose, cheeks, and chin, or on the legs, in particular on the upper thigh, below the knee joint, and around the ankles. Reticular veins are also known as feeder veins and are dilated veins that appear bluish or greenish in colour and are visible to the naked eye. Spider and reticular veins generally consist of small, thin, dark-colour veins that lie close to the surface of the skin. Usually they measure only a few millimeters. They often have a web or sunburst pattern, but may also appear as random line segments. Varicose veins are larger than spider veins and can appear as swollen, twisted veins that lie just under skin. They are typically 3 millimeters (mm) or more in diameter. Varicose veins are most commonly found on the leg, although varicose veins can occur elsewhere on the body and usually have a blue or purple colour and may protrude above the surface of the skin. These veins have usually lost their ability to carry blood back to the heart and blood often accumulates in these veins.

A number of factors can contribute to the development of varicose and spider veins, including heredity, obesity, posture, hormonal shifts, excessive heat, and standing or sitting for a long period of time.

Reticular and varicose veins may cause patients to experience symptoms such as aching, burning, swelling, cramping, and itching. More serious complications of varicose veins can include thrombophlebitis, dermatitis, haemorrhage, and ulcers. If certain varicose veins are not treated, blood clots may form in the vein, and phlebitis or inflammation of the inside lining of the vein may occur. Equally, many patients seek medical treatment of varicose veins and spider veins for cosmetic reasons.

Various approaches have been developed to treat spider, reticular and varicose veins. These treatments include vein removal for severe cases, using for example techniques such as ambulatory phlebotomy or vein stripping. Such operations can be painful and uncomfortable for patients following the surgery.

Endovenous laser and radiofrequency ablation are also known methods of treatment. These methods require specialized training for practitioners and expensive equipment. Follow-up treatment for smaller branch varicose veins is also often needed in the weeks after the initial procedure. Complications for radiofrequency ablation and endovenous laser treatment include bruising, burns and paranesthesia.

Sclerotherapy is another well-known treatment for smaller varicose and spider veins lying close to the surface of the skin. In this procedure, the affected veins are injected with a sclerosing solution, such as sodium tetradecyl sulfate (STS). The sclerosing solution causes inflammation and subsequent sclerosis of the vein. The sclerosis results in localized scarring of the veins, which forces re-routing of the blood away from the affected veins. When treating veins with a sclerosing solution, the sclerosing solution may not stay in the desired portion of the vein being treated and may leak outside of the vein, causing skin ulcerations. Hyperpigmentation may also occur as a result of the leakage of a blood component, hemosiderin pigment, from the treated vein. The sclerosing solution can also cause inflammation in the region where the solution was injected.

Microwave ablation is an endovenous treatment meaning that the treatment probe is inserted into the vein during treatment. Currently, most of the ablation antennas are basically dipole or monopole antennas. Those antennas require a length closer to a quarter wavelength to maximize the radiation efficiency. Such antennas are normally made from coaxial cables with the outer conductor that stripped off in the radiator portion, such that the exposed core and the insulation are relatively week both mechanically and electrically and are subject to risky damages, such as for example, the week mechanical strength may result in mechanical breakdown and therefore it has to be protected by placing it inside a dielectric casing. In addition, the induced current in the core may burn out conductor during the operations. These possible risks are the one of the obstacles to the popularization of the microwave ablation treatment.

SUMMARY OF THE INVENTION

In one aspect a probe for microwave ablation is provided. The probe comprises a feed coaxial cable and an antenna that includes an outer housing having a predetermined diameter and a predetermined length to define an inner cavity therein with a radiating conductor with matched stepped portion positioned in the cavity and a dielectric material placed in the cavity and configured to cover the radiating conductor with matched stepped portion and provide insulation between the radiating conductor and the outer housing. The matching stepped portion is formed at one end of the radiating conductor and is coupled to the housing in proximity to the radiating head. An opposite end of the radiating conductor is secured to the inner conductor of the feed coaxial rod. The probe further comprises a microwave generator connector configured to connect to a microwave generator that generates an electromagnetic energy that is transmitted to the antenna by the feed coaxial cable. The stepped portion of the radiating conductor and the antenna's dielectric material covering increase antenna's mechanical strength to withstand higher temperatures and allow a good impedance match between the antenna and the feed cable.

In addition to the aspects and embodiments described above, further aspects and embodiments will become apparent by reference to the drawings and study of the following detailed description.

BRIEF DESCRIPTION OF THE DRAWINGS

Throughout the drawings, reference numbers may be re-used to indicate correspondence between referenced ele

DETAILED DESCRIPTION OF SPECIFIC EMBODIMENTS

The present invention relates generally to surgical apparatus for microwave ablation and more particularly, to an apparatus and methods for treatment of unwanted varicose, reticular and spider veins in a venous system of a patient. Some microwave ablation applications, such as the varicose vein, require a flexible applicator to reach certain targets through a curved path, so the diameter of the probe can be in different sizes to fit different ablation applications in the varicose veins or the spider veins. Since the ablation of the varicose vein normally doesn't use the water-cooling techniques to reduce the temperature of a feed coaxial cable, the radiation efficiency of the probe's antenna must be increased so that a microwave generator with lower power can be used.

During the thermal ablation the targeted tissue regions are heated to ablative temperatures while the non-targeted tissue regions are not affected or damaged. In general, the microwave ablation probes comprise a feeding cable terminated by a radiating antenna so that the electric field radiated by the antenna is absorbed in surrounding tissue leading to heating such tissue. Typically, current travels toward the antenna on the inner conductor surface and inside surface of the outer conductor of the feed coaxial cable. A part of the current can travel back toward the microwave generator on the outer surface of the outer conductor due to impedance mismatch between the antenna and the feed coaxial cable and the unbalanced structure of the cable. Such reflected current can generate unwanted heat along the feed coaxial cable and decreases the efficiency of the ablation probe.

Because the feeding cable is made of conductors and dielectric materials, it can heat up when the microwave electromagnetic energy supplied from the microwave generator passes through there. The geometry of the radiating antenna determines the probe's efficiency at transferring power from the feeding cable to the radiating antenna.

Inefficient microwave ablation probes will require larger power applied to the feeding cable to achieve the same ablation as an efficient probe. Power attenuation within the feeding cable leads to heating of the feeding cable, therefore, highly efficient probes are desirable. In addition, in some applications, the microwave ablation applicators (probes) need to reach targets through a curved path, so the diameter of the probe needs to be in sizes that are fit to reach curved channels.

Figure 1:
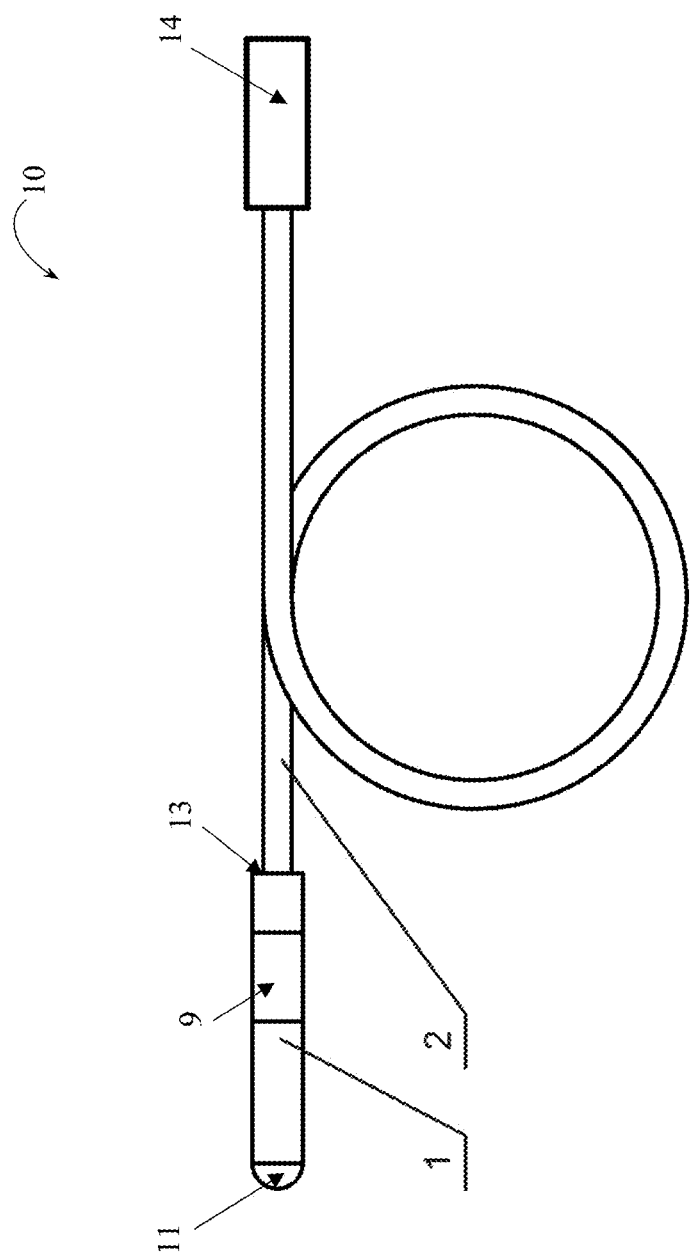
- FIG. 1 is a schematic view of an example of a probe for microwave ablation.

Referring now to FIG. 1, an example of a probe 10 for microwave ablation per the present invention is illustrated. The probe 10 includes a radiating antenna 1 having a radiating head 11 at a distal end and a feed coaxial cable 2 connected to the antenna 1 at a proximal end 13 of the antenna 1. The feed coaxial cable 2 has an inner conductor 12 (see FIG. 2) and an outer conductor 16, with a dielectric material 17 between the inner conductor and the outer conductor of the coaxial cable 2, and an outer jacket enveloping the outer conductor of the coaxial cable 2. A distal end of the coaxial cable 2 is connect to a microwave generator through a connector 14. The microwave generator uses a power source, such as for example a magnetron, and can provide for example 100 watts of microwave electromagnetic energy of a frequency of 2.45±0.05 GHz range. The feed coaxial cable 2 can been semirigid (partially flexible) so that the antenna 1 can be inserted into the tubular channels of the patients, such as veins.

Figure 2:
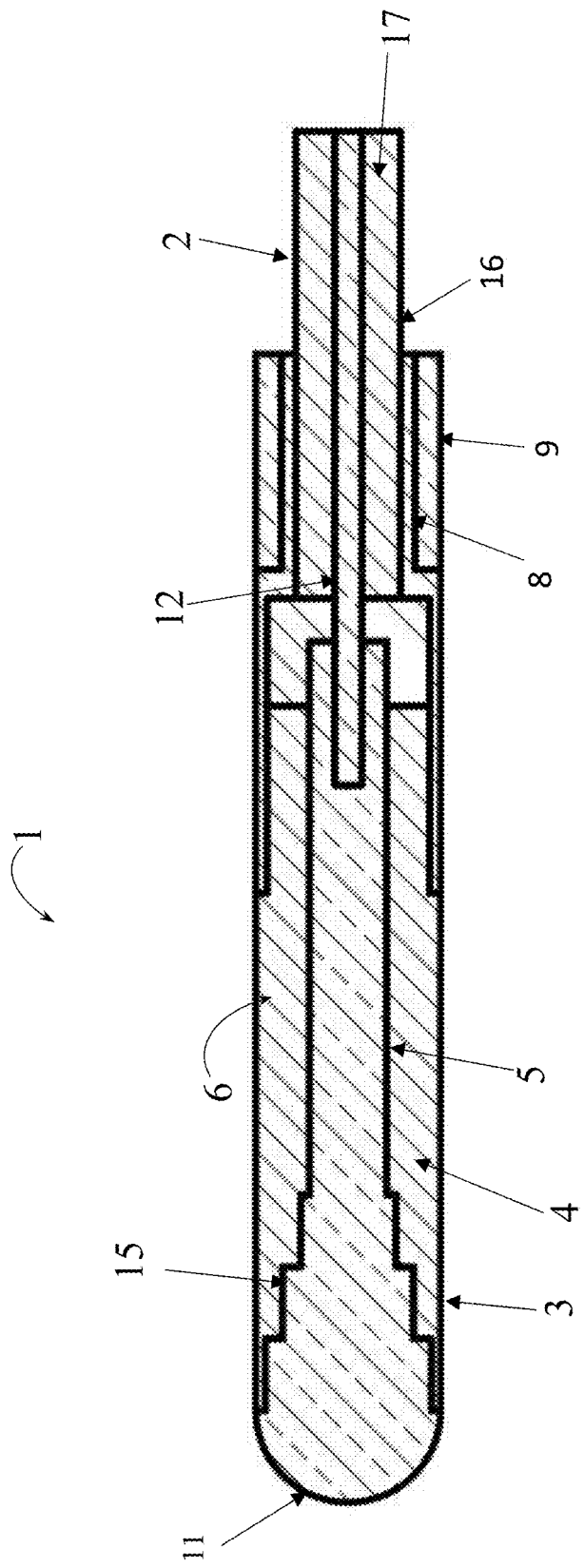
FIG. 2 is a cross-sectional side view of an example of an antenna of a microwave ablation probe.

FIG. 2 illustrates an example of the radiating antenna 1. The antenna 1 can comprise an outer housing 3 of a predetermined diameter and a predetermined length. The outer housing 3 of the antenna 1 can be elongated defining a coaxial cavity 6 therein. The coaxial cavity 6 is the resonant cavity of the ablation probe 10 and its geometry is important since it determines the output frequency of the generated energy. A radiating conductor 5 can be positioned in the cavity 6. The radiating conductor 5 comprises a radiating matching steps portion 15 formed at one end and coupled to the housing 3 in proximity to the radiating head 11. An opposite end of the radiating conductor 5 is fixed to the inner conductor 12 of the feed coaxial rod 2. A dielectric material 4 is positioned in the cavity 6 covering the radiating conductor 5 with matching steps 15 of the antenna 1. The dielectric material 4 feels the coaxial cavity 6 providing mechanical strength to the antenna 1 and acts as a waveguide for the electromagnetic energy in the radiating antenna 1 as well as an insulator between the radiating conductor 5 and the housing 3 of the antenna 1. The radiating conductor 5 of the antenna 1 is secured to the inner conductor 12 of the feed coaxial cable 2 using an epoxy resin 7. The proximal end 13 of the radiating antenna 1 can have a reduced diameter 8 so that it may fit into a proximal end of the feed coaxial cable 2. A fastener, such as for example, a fastening ring 9 can be placed outside of the outer jacket of the feed coaxial cable 2 to ensure a firm connection between the feed cable 2 and the antenna 1.

The design of the radiating antenna 1 of the present invention with the coaxial cavity 6 and radiating conductor 5 with matching stepped portion 15 increases the diameter of the radiating conductor 5 of the antenna 1 to be greater than that of the core (inner conductor 12) of the feed coaxial cable 2 therefore prevents the burn out due to the overheating of the core 12 of the feed coaxial cable 2. A number of the steps in the stepped portion 15 depends on the diameter of the antenna 1. For example, more steps of radiation element 15 will be used for probe 10 with larger diameters while less steps will be used in probe 10 with smaller diameter. For example, the number of steps of the radiating portion 15 of the radiating conductor 5 can be between 2-6 steps, and most preferably between 3-5 steps.

The increased diameter of the radiating conductor 5 covered with the dielectric material 4 also increases the mechanical strength of the antenna 1. Last but not least, by using stepped structure of the radiating conductor 5 with dielectric materials 4, multiple, serially connected, quarter-wave dielectric portions are formed that are used to vary the impedance of the antenna 1 to obtain a good match with the impedances between the antenna 1 and the feed coaxial cable 2 so that a shorter antenna can be used without sacrificing the efficiency of the probe 10. Having an antenna 1 with a smaller length than the monopole or the dipole antennas ordinarily used in the art, one can use the probe 10 of the present invention for curved paths, such as for examples, through curved venous paths. In addition, due to the good impedance match between the antenna 1 and the feeding cable 2, the probe 10 has low reflection back to the power source (the microwave generator), therefore a voltage standing wave ratio (VSWR) of less than 1.1 can be achieved.

The length of the antenna 1 can be between 2-10 mm while the diameter of the antenna 1 can be between 1-3.5 mm, so that it can fit in the different tubular channels (e.g., veins) inside the human body.

The radiating head 11 of the antenna 1 can be semi-spherical and is configures such that the generated electromagnetic energy is radiated there through. The antenna's design with semi-spherical head 11 allows to achieve a more spherical ablation pattern. In one embodiment, the housing 3 of the antenna 1 and the semi-spherical head 11 can be made of any suitable metal. For example, the housing 3 of the antenna 1 and the semi-spherical head 11 can be made of a non-magnetic metals or alloys, such as for example, a titanium, an aluminum, bronze or gold- or silver-plated materials to allow real time visualization under Magnetic Resonance Imaging (MM). In one implementation, the head 11 of the antenna 1 can be sharpened at the tip.

The dielectric material 4 in the antenna's coaxial cavity 6 can be a polytetrafluoroethylene (PTFE), a polyamide, an alumina, a ceramic or any other suitable dielectric material that can provide protection and mechanical stability of the probe 10 as well as improve the power coupling to the tissue to be ablated. The antenna radiating conductor 5 and its stepped portion 15 are designed to fit within the dielectric material 4. In addition, the dielectric material 4 acts as an insulator between the radiating conductor 5 and the outer housing 3 of the antenna 1.

In one implementation, an entire outside surface of the antenna 1 (outer surface of the housing 3) is coated with a dielectric material, such as for example, a PTFE coating to reduce the stickiness of the probe 10 during the ablation process, without using an additional dielectric casing.

Figure 3:
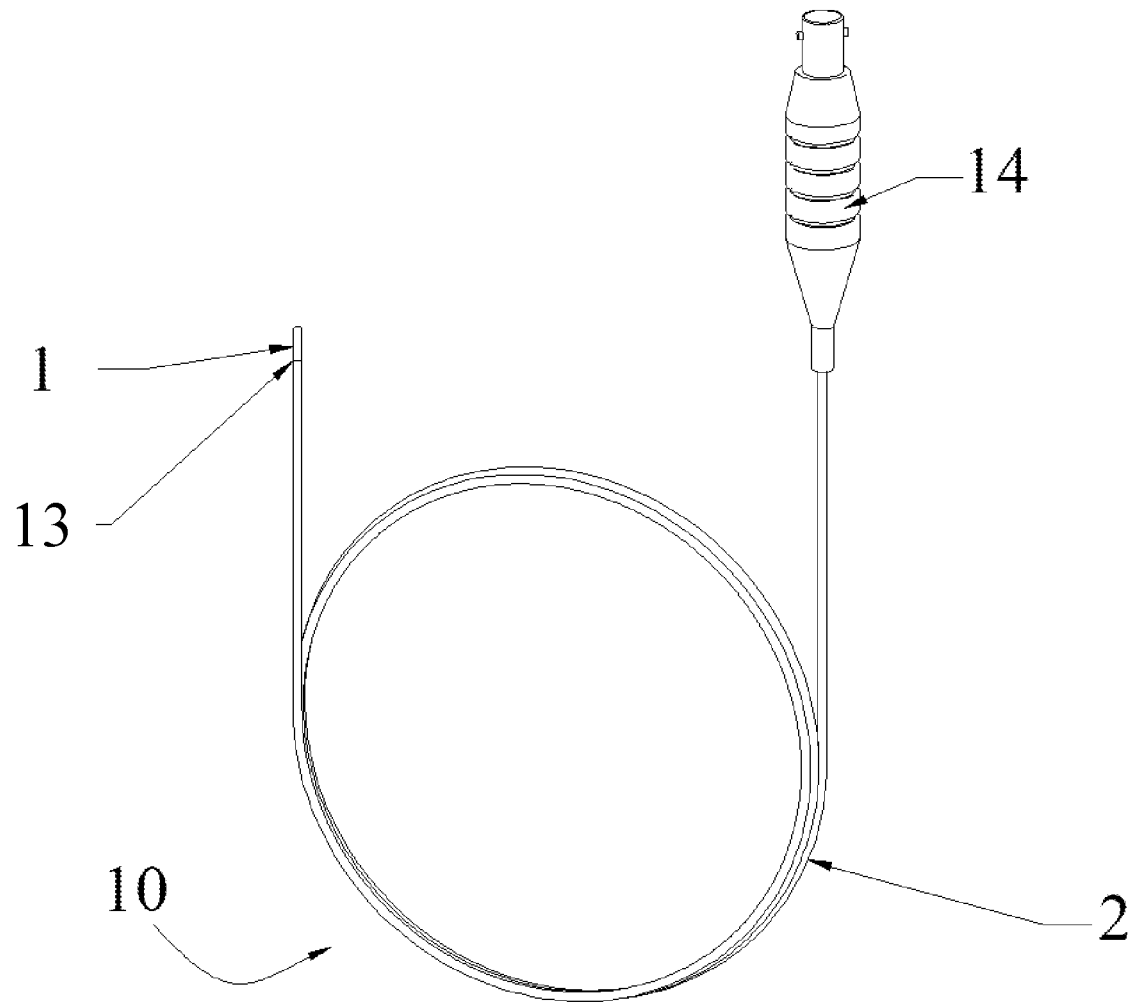
FIG. 3 is a photograph of an example of a probe for microwave ablation.

FIG. 3 is a photograph of an example of the microwave ablation probe 10 of the present invention showing the antenna 1 and the flexible feed coaxial cable 2 connected to the antenna 1 at the proximal end 13. The feeding coaxial cable 2 can further comprise the connector 14 at its distal end configured to fit to an output connector of the microwave generator (not shown).

The flexible feed coaxial cable 2 can be made of a flexible plastic, such as a polyurethane, polyethylene, polypropylene, poly vinyl chloride, fluorinated ethylene propylene polymer, silicone materials or any other suitable material. In some implementations, a coating, such as for example, a silicon elastomer coating or a hydrophilic polymer coating, can be used. For example, a PTFE coated latex can be used over the feed coaxial cable 2. The antenna 1 (the rigid applicator) of the probe 10 can be made of non-magnetic metals or alloys, such as for example, a titanium, an aluminum, bronze or gold- or silver-plated materials, to allow real time visualization under Magnetic Resonance Imaging (MRI). A coating, such as a silicon elastomer coating or a hydrophilic polymer coating, can also be used. For example, a PTFE coated latex may be used.

The length of both rigid applicator (the antenna 1) and the flexible applicator (feed cable 2) can be custom manufactured to fit any lengths of different tubular channels, such as various lengths of varicose vein, reticular vein or spider veins. Customized lengths will be calibrated so that the energy delivered at the radiating head 11 of the antenna 1 will be reliably constant.

In one method of operation, the probe 10 is introduced into the vein, along its length, such that the head 11 of the probe 10 is located at or near the distal end of the vein. The vein may be in any part of the patient's body, and typically it is in the patient's leg. For example, the vein can be the leg and below the knee. The probe 10 is then withdrawn from the distal end of the vein towards the proximal end of the vein, with ablation energy being introduced into the vein from the head 11 of the probe 10 as the probe is withdrawn. The position of the introduced probe 10 before the treatment is registered with ultrasound and RF guidance of the monitoring system. As the probe 10 is withdrawn the rate of withdrawal is recorded in the microwave generator (or any other processing unit coupled to the probe 10) and is transferred either wirelessly or by wires, through cable connections, or post treatment memory devices to a web-based data storage application.

In one implementation, the probe 10 of the present invention can be used in treatment of undesired varicose vein in a venous system of a patient. The method for treating varicose veins can comprise the steps of introducing percutaneously and trans-luminally a flexible, atraumatic microwave probe 10 to the distal end of the varicose vein, applying a low-temperature, microwave energy of 100 watts at a frequency of about 2.45±0.05 GHz range through the head 11 of the antenna 1, moving the microwave probe 10 at a specific rate of withdrawal from the distal to proximal end of the varicose vein to safely and effectively coagulate and dehydrate the varicose vein. In one implementation, when the probe 10 is used for treating a reticular or spider vein in a venous system of a patient, the distal end of the antenna 1 can be rigid and sharpened. The method for treating reticular or spider vein can comprise the steps of introducing percutaneously the rigid, sharpened head of the microwave probe 10 in close proximity to the distal end of the varicose vein, applying a low-temperature, microwave energy at a frequency of 2.45±0.05 GHz range through the sharpened tip of the antenna, and then moving the microwave probe 10 at a specific rate to effect adequate treatment of the culprit vein. In some implementations, the probe 10 of the present invention can be used in treatment of solid tumors, such as thyroid tumor, lung cancer, liver cancer or any other tumors where operative treatment is not available.

While particular elements, embodiments and applications of the present disclosure have been shown and described, it will be understood, that the scope of the disclosure is not limited thereto, since modifications can be made by those skilled in the art without departing from the scope of the present disclosure, particularly in light of the foregoing teachings. Thus, for example, in any method or process disclosed herein, the acts or operations making up the method/process may be performed in any suitable sequence and are not necessarily limited to any particular disclosed sequence. Elements and components can be configured or arranged differently, combined, and/or eliminated in various embodiments. The various features and processes described above may be used independently of one another, or may be combined in various ways. All possible combinations and sub-combinations are intended to fall within the scope of this disclosure. Reference throughout this disclosure to "some embodiments," "an embodiment," or the like, means that a particular feature, structure, step, process, or characteristic described in connection with the embodiment is included in at least one embodiment. Thus, appearances of the phrases "in some embodiments," "in an embodiment," or the like, throughout this disclosure are not necessarily all referring to the same embodiment and may refer to one or more of the same or different embodiments.

Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without operator input or prompting, whether these features, elements and/or steps are included or are to be performed in any particular embodiment. No single feature or group of features is required for or indispensable to any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The example calculations, simulations, results, graphs, values, and parameters of the embodiments described herein are intended to illustrate and not to limit the disclosed embodiments. Other embodiments can be configured and/or operated differently than the illustrative examples described herein.

The invention claimed is:

1. A probe for microwave ablation comprising:
a feed coaxial cable having an inner conductor, an outer conductor and a dielectric material therein between the inner conductor and the outer conductor of the feed coaxial cable;
an antenna comprising:
an outer housing having a predetermined diameter and a predetermined length, the outer housing defining an inner coaxial cavity therein, the housing having a radiating head at a distal end and a proximal end configured to be secured to a proximal end of the feed coaxial cable;
a radiating conductor positioned in the inner coaxial cavity and comprising a stepped portion formed at a distal end of the radiating conductor coupled to the housing in proximity to the radiating head, the radiating conductor is secured to the inner conductor of the feed coaxial cable at an opposite proximal end, a diameter of a step of the stepped portion in proximity to the radiating head being biggest, a diameter of each step of the stepped portion away from the radiating head being smaller than the step in proximity to the radiation head, a diameter of the stepped portion of the radiating conductor closest to the opposite proximal end of the radiating conductor being smallest; and
a dielectric material placed in the inner coaxial cavity and configured to cover the radiating conductor with the stepped portion and provide insulation between the radiating conductor and the outer housing, the stepped portion of the radiating conductor with the antenna's dielectric material forming multiple, serially connected, quarter-wave dielectric portions, wherein the multiple, serially connected, quarter-wave dielectric portions are used to vary the impedances of the antenna to obtain matching impedance between the antenna and the feed coaxial cable; and
a microwave generator connector configured to connect to a microwave generator that generates an electromagnetic energy that is transmitted to the antenna by the feed coaxial cable,
wherein the stepped portion of the radiating conductor with the antenna's dielectric material covering increase antenna's mechanical strength to withstand higher temperatures and allow a good impedance match between the antenna and the feed cable.

2. The probe for microwave ablation of claim 1, wherein the radiating head of the outer housing of the antenna has a semi-spherical shape, the generated electromagnetic energy is radiated out through the radiating head.

3. The probe for microwave ablation of claim 1, wherein a voltage standing wave ratio (VSWR) is less than 1.1.

4. The probe for microwave ablation of claim 1, wherein a diameter of the antenna is between 1 mm to 3.5 mm.

5. The probe for microwave ablation of claim 1, wherein a length of the antenna is between 2 mm to 10 mm.

6. The probe for microwave ablation of claim 1, wherein the dielectric material in the antenna is selected form a polytetrafluoroethylene (PTFE), polyamide, alumina or ceramic.

7. The probe for microwave ablation of claim 1, wherein an outside surface of the antenna's housing is coated with a PTFE coating.

8. The probe for microwave ablation of claim 1, further comprising an epoxy resin to secure the radiation conductor to the inner conductor of the feed coaxial cable.

9. The probe for microwave ablation of claim 8, further comprising a fastening ring to firmly connect the antenna to the feed coaxial cable.

10. The probe for microwave ablation of claim 1, wherein a number of steps in the stepped portion of the radiating conductor is between 2-6, preferably 3-5.

11. The probe for microwave ablation of claim 1, wherein a diameter of the radiation conductor at the proximal end is reduced to fit into the feed coaxial cable.

12. The probe for microwave ablation of claim 1, wherein the electromagnetic energy generated by the microwave generator is about 100 watts at a frequency of 2.45±0.05 GHz range.

13. Use of the probe for microwave ablation of claim 1 for a treatment of varicose, reticular and spider veins.

14. Use of the probe for microwave ablation of claim 1 for a treatment of solid tumors.

* * * * *